United States Patent [19]

Wakabayashi et al.

[11] Patent Number: 5,410,035

[45] Date of Patent: Apr. 25, 1995

[54] FOOD COMPOSITION HAVING HYPOTENSIVE EFFECT

[75] Inventors: Shigeru Wakabayashi; Kazuhiro Ohkuma, both of Sanda; Yoshimi Mochizuki, Itami, all of Japan

[73] Assignee: Matsutani Chemical Industries Co., Ltd., Hyogo, Japan

[21] Appl. No.: 51,279

[22] Filed: Apr. 23, 1993

Related U.S. Application Data

[63] Continuation of Ser. No. 914,004, Jul. 16, 1992, abandoned, which is a continuation of Ser. No. 729,729, Jul. 15, 1991, abandoned.

[30] Foreign Application Priority Data

Aug. 7, 1990 [JP] Japan .................................. 2-209732

[51] Int. Cl.⁶ ......................... C08B 37/16; A23G 3/00
[52] U.S. Cl. ..................... 536/103; 426/658; 426/660
[58] Field of Search ................ 536/103; 426/658, 660

[56] References Cited

U.S. PATENT DOCUMENTS 4,219,580 8/1980 Torres .................................. 426/549
4,247,568 1/1981 Carrington et al. ................ 536/110
4,510,166 4/1985 Lenchin et al. ..................... 536/103

FOREIGN PATENT DOCUMENTS 0368451 5/1990 European Pat. Off. .

OTHER PUBLICATIONS

Database WPIL/Derwent An=86–091021 DW=8614, Derwent Publications Ltd., London, GB.
Chemical Abstracts, vol. 103, Jul. 29, 1985, Columbus, Ohio, No. 36579e.

*Primary Examiner*—Nathan M. Nutter
*Attorney, Agent, or Firm*—Sughrue, Mion, Zinn, Macpeak & Seas

[57] ABSTRACT

A food or feed having an indigestible dextrin exhibits a hypotensive effect.

9 Claims, No Drawings

FOOD COMPOSITION HAVING HYPOTENSIVE EFFECT

This is a continuation of application Ser. No. 07/914,004, filed Jul. 16, 1992, now abandoned, which is a continuation of application Ser. No. 07/729,729, filed Jul. 15, 1991, now abandoned.

BACKGROUND OF THE INVENTION

1. Field of the Invention

The present invention relates to food compositions or feed compositions having a hypotensive effect and therefore very useful for preventing hypertension.

2. Description of the Prior Art

Hypertension is thought attributable to a tangle of genetic factors and other factors, such as dietary factors including excessive intake of salt and obesity, and constitutional or renal factors and endocrine nerve factors including hyperlipidemia, while more than 90% of hypertensives are said to be affected with essential hypertension, the etiology of which has yet to be determined definitely.

It is known that when the human body remains hypertensive for a long period of time, the vascular system undergoes pathological changes, especially cerebral, cardiac or renal arteriosclerosis. Arteriosclerosis, once becoming persistent, is no longer easy to cure and further leads to aggravated hypertension in a vicious cycle.

Although sedatives or hypotensive drugs are used for symptomatic therapy to treat hypertension, the possible side effect is suspected. Accordingly, attempts are made in preference to lower blood pressure by improvements in the living environment as by alimentotherapy and removal of stress.

The fundamental principles of alimentotherapy are said to be salt restriction, intake of sufficient quantities of proteins from dishes seasoned lightly, intake of milk, vegetables, seaweeds, fruits and the like, restriction of oils and fats to be taken to those of vegetable origin, intake of dietary fibers and refraining from eating out. Among these, dietary fibers are divided generally into insoluble fibers and those soluble in water. The former include cellulose, lignin, hemicelluloses A and C, chitin, collagen, etc. Examples of the latter are pectin, guar gum, mannans of devil's-tongues, sodium alginate, carageenan, agar, carboxymethlcellulose, indigestible dextrin, polydextrose and the like.

Although it has been found that these dietary fibers have a relationship with cancer of the colon, diabetes, hypercholesterolemia, biliary calculus, etc., they have not been fully investigated in connection with hypertension except that the alginate is known to be effective for removing sodium. In this connection, it is said that obesity can be obviated or prevented effectively by ingesting foods which contain hemicellulose extracted from grains or beans or polysaccharides such as pectic substances, guar gum and polydextrose.

SUMMARY OF THE INVENTION

An object of the present invention is to newly develop a food having a hypotensive effect.

Another object of the invention is to newly develop a food having a hypotensive effect afforded by using an indigestible dextrin which is a kind of water-soluble dietary fiber.

Other objects of the invention will become apparent from the following description.

We have conducted research on the physiological activity of indigestible dextrins which are water-soluble dietary fibers and developed new food compositions based on the finding that these dextrins have effects to ameliorate the intestinal function, to alleviate hypercholesterolemia and to lower insulin requirements. We have further found that the dextrins of the type mentioned have a hypotensive effect and accomplished the present invention.

More specifically, we have found that food compositions having a hypotensive effect can be prepared by incorporating into a food an indigestible dextrin which is the indigestible component of pyrodextrin obtained by refining pyrodextrin or which is obtained by concentrating the indigestible component, although pyrodextrin was conventionally almost in no way regarded as a food material.

Whereas much attention has been directed to dietary fibers in recent years, insoluble fibers, which are not nutritive, were in the past removed as residues in food production processes to the greatest possible extent. Based on the research conducted throughout the world on the relations between components of foods and diseases in recent years, the dietary fiber has been defined as "including all indigestible components of foods which can not be digested with human digestive enzymes." The term "dietary fiber" is used herein also in conformity with this definition and includes water-soluble fibers, insoluble fibers, etc., i.e., all of those as defined above. Examples of dietary fibers are as follows.

Water-soluble fibers:
  pectin, guar gum, mannans of devil's-tongues, sodium alginate, carageenan, etc.

Water-insoluble fibers:
  cellulose, lignin, hemicellulose, chitin, collagen etc.

Based on the research so far conducted, many publications or reports have been made about the intake of dietary fibers. It is reported that the intake by Japanese has reduced greatly. For example, the daily intake of 23g in the past has decreased to 18 g/day.

The indigestible dextrins for use in the present invention are divided into three general categories.
  (i) A dextrin prepared by treating pyrodextrin with at least one of $\alpha$-amylase, $\beta$-amylase and glucoamylase, and refining the resulting dextrin with activated carbon, ion exchange resins or the like.
  (ii) A dextrin prepared by fractionating the dextrin (i) using an ion exchange resin to obtain a concentrated indigestible component.
  (iii) A dextrin obtained by hydrogenating the dextrin (i) or (ii).

Unexamined Japanese Patent Publications 1990-100695, 1990-145169 and 1990-154664 disclose these types of dextrins (i) to (iii), which are all included within the scope of the present invention.

Stated more specifically, the processes disclosed in these published inventions include the following examples.
  (a) A process for preparing an indigestible dextrin characterized by dissolving pyrodextrin in water, causing $\alpha$-amylase to act on the solution and subsequently causing transglucosidase to act thereon, in the presence of $\beta$-amylase when required.
  (b) A process as set forth in paragraph (a) wherein the pyrodextrin used in one prepared by roasting in the usual manner starch singly or a mixture of starch and at least one of a monosaccharide and an oligosaccharide.

(c) A process for preparing a dextrin containing dietary fiber characterized by dissolving pyrodextrin in water and causing α-amylase to act on the solution.

(d) A process as set forth in paragraph (c) which is characterized by hydrogenating the solution after causing the α-amylase to act thereon.

(e) A process as set forth in paragraph (c) wherein transglucosidase and/or β-amylase are/is caused to act on the solution before hydrogenation after the α-amylase has been caused to act thereon.

(f) A process as set forth in any one of paragraphs (c) to (e) wherein the pyrodextrin used is one prepared by roasting in the usual manner starch singly or a mixture of starch and at least one of a monosaccharide and an oligosaccharide.

(g) A process for preparing a dextrin having a high dietary fiber content characterized by causing α-amylase to act on pyrodextrin, then causing glucoamylase to act on the resulting mixture, followed by filtration, decolorization and desalting to obtain a dextrin solution of high purity, subsequently separating a dextrin fraction from the solution by chromatography using a strongly acidic cation exchange resin, and collecting a dietary fiber from the fraction.

(h) A process as set forth in paragraph (g) wherein transglucosidase is caused to act on the mixture before the filtration, decolorization and desalting after the glucoamylase has been caused to act thereon.

(i) A process wherein the dextrin of high dietary fiber content prepared by the process (g) or (h) is hydrogenated.

These processes are described in detail in the specifications of the above publications and are useful in practicing the present invention.

Although the composition of the present invention exhibits a hypotensive effect insofar as it contains the indigestible dextrin, the composition contains the dextrin preferably in an amount of up to 20g by weight. This amount is not absolute but is suitably variable in accordance with the intake of the food composition and the condition of the person who is to take the composition.

The food for use in the invention includes a wide variety of foods, typical of which are, for example, beverages, cakes, dressings for frozen cakes, pastelike marine products, etc. The dextrin can be incorporated also in feeds for animals.

EMBODIMENTS

The present invention will be described in greater detail with reference to reference examples, i.e., preparation examples of indigestible dextrins, and examples, in which the parts are by weight.

REFERENCE EXAMPLE 1

On 1.0 kg of commercial potato starch was sprayed 50 ml of 1.0% hydrochloric acid solution using pressurized air. The starch was then uniformly stirred, thereafter placed into an aluminum vat, pre-dried in a dryer at 100° C. for 1 hour and subsequently roasted at 150° C. for 3 hours. The pyrodextrin obtained was 6.8 in DE, 160 cps in viscosity (concentration 50%, 30° C.) and 57% in indigestible dextrin content.

A 1.0 kg quantity of hot water was added to 1.0 kg of the pyrodextrin thus prepared, and the solution was neutralized with 1N sodium hydroxide to a pH of 5.8. To the solution was added 0.1 % of α-amylase (Termamyl 120L, product of Novo Industry Co., Ltd.) to effect a reaction at 95° C. for 1 hour. The reaction mixture was thereafter heated to 115° C. to complete the reaction. The reaction mixture was then adjusted to a pH of 5.5 and a temperature 55° C., and 0.05% of β-amylase (product of Amano Seiyaku Co., Ltd.) and 0.1% of transglucosidase (product of Amano Seiyaku Co., Ltd.) were added to and reacted with the mixture for 24 hours to obtain a dextrin having the following sugar composition.

15.8% of DP1, 10.7% of DP2 (0.6% of maltose, 0.3% of Kojibiose and 9.8% of isomaltose), 5.3% of DP3 and 68.2% of DP4 and higher oligosaccharides.

The dextrin solution was further refined and concentrated in the usual manner using activated carbon and ion exchange resin, and the product was dried by a spray dryer to obtain a powder.

REFERENCE EXAMPLE 2

A 5,000 kg of commercial potato starch was placed into a ribbon mixer, 150 liters of 1.0% hydrochloric acid was sprayed on the starch with stirring, and the mixture was subsequently passed through a mixer to prepare a uniform mixture, which was then aged in the ribbon mixer for 5 hours. The mixture was pre-dried by a flush dryer to a water content of 3%, thereafter continuously placed into a roaster of the rotary kiln type and roasted at 180° C. for 2 hours.

To 2,000 kg of the pyrodextrin obtained by the above method was added 4,000 liters of water, and the solution was adjusted to a pH of 6.0 and hydrolyzed with 0.2% of α-amylase (Termamyl 60L, product of Novo Industry Co., Ltd.) at 95° C. for 1 hour. The reaction mixture was decolorized, refined, for example, by desalting with an ion exchange resins and dried by a spray dryer, giving 1700 kg of a powder. The refined product of pyrodextrin thus obtained was found to contain 35% of dietary fiber as quantitatively determined by the Proskey-AOAC method.

REFERENCE EXAMPLE 3

A 10 kg quantity of pyrodextrin (Arabix #7, product of Matsutani Chemical Industries, Co., Ltd.) was dissolved in 20 kg of water, the solution was adjusted to a pH of 5.5, and 0.2 wt. % of α-amylase (Klaistase, product of Daiwa Kasei Co., Ltd.) was added to the solution to effect a reaction at 85° C. for 1 hour. The reaction mixture was then maintained at a temperature of 120° C. for 15 minutes to deactivate the amylase, cooled to a temperature of 55° C., adjusted to a pH of 4.5 and reacted with 0.1 wt. % of glucoamylase (product of Amano Seiyaku Co., Ltd.) to effect saccharification for 36 hours, whereupon the reaction mixture was adjusted to a pH of 3.5 to deactivate the glucoamylase. The mixture was then purified using activated carbon and ion exchange resins and thereafter concentrated, giving 1.5 kg of 50% solution. The solution had the sugar composition of 51.2% of glucose, 2.2% of disaccharide, 3.9% of trisaccharide, and 42.8% of tetrasaccharide and higher oligosaccharides.

A 100 ml quantity of the solution was passed at SV=0.25 through a column packed with 5 liters of XFS-43279.00 (product of Dow Chemical, Japan) which is a strongly acidic cation exchange resin of the alkali metal type. Water was then passed through the column to collect a high-molecular-weight dextrin. The sugar composition of the product was 4.4% of glucose, 1.2% of disaccharide, 1.7% of trisaccharide and 92.1% of tetrasaccharide. The dextrin was 83.9% in dietary fiber content as determined by the Proskey-AOAC method. The product was further treated in the same manner as in Reference Example 1 to obtain a powder.

EXAMPLES 1 AND 2

Male rats initially weighing about 300g and spontaneously developing hypertension (17-week-old, provided by Hoshino Test Animal Farm) were preliminarily raised in groups, five rats in each group, then fed on a feed containing an indigestible dextrin of the invention or on a basic feed (AIN prescription) for 15 days, and checked for blood pressure and total blood cholesterol with time. The feed for the dextrin containing groups was changed to the basic feed further until 27th day. The compositions of the feeds were listed in Table 1, and the test results in Tables 2 and 3.

TABLE 1

|  | Control | Ex. 1 | Ex. 2 |
|---|---|---|---|
| Casein | 22.00 | 22.00 | 22.00 |
| Lard | 10.00 | 10.00 | 10.00 |
| Mineral mixture | 3.50 | 3.50 | 3.50 |
| Vitamin mixture | 1.00 | 1.00 | 1.00 |
| Choline hydrogen tartrate | 0.20 | 0.20 | 0.20 |
| NaCl | 1.00 | 1.00 | 1.00 |
| Cellulose | 3.00 | 3.00 | 3.00 |
| Maltose | 59.30 | 56.30 | 56.30 |
| Indigestible dextrin of Reference Example 1 | — | 3.00 | — |
| Indigestible dextrin of Reference Example 3 | — | — | 3.00 |
| Total | 100.00 | 100.00 | 100.00 |

TABLE 2

| Variations in Blood Pressure (unit: mmHg) | | | | | |
|---|---|---|---|---|---|
|  | Before test | 5th day | 10th day | 15th day | 27th day |
| Control | 196 | 196 | 196.8 | 199.9 | 206.7 |
| Example 1 | 195.8 | 185.7 | 184.4 | 183.6 | 196.3 |
| Example 2 | 195.9 | 191.6 | 189.6 | 186.5 | 207.4 |

TABLE 3

| Total Blood Cholesterol (unit: mg/dl) | | | |
|---|---|---|---|
|  | Before test | 8th day | 15th day |
| Control | 72 | 106.1 | 117.9 |
| Example 1 | 72 | 97.3 | 106.4 |
| Example 2 | 72 | 84.5 | 98.1 |

Table 2 reveals that the rats raised with the dextrin-containing feed of the invention exhibited a significantly lower blood pressure value than the control group on the 15th day, and higher blood pressure after the change of feed to the basic feed on the 27th day. Table 3 shows that the rats raised with the dextrin-containing feed of the invention were lower in total blood cholesterol value than the control group on the 8th day and the 15th day. These rats were comparable to the control group in feed intake and weight changes. This indicates that the dextrin-containing feeds were satisfactorily usable with safety.

EXAMPLE 3

A carbonated beverage composition which can be taken as a food for alimentotherapy for a prolonged period of time was prepared according to the following formulation.

| Indigestible dextrin of Reference Example 1 | 50 parts |
|---|---|
| Granulated sugar | 125 parts |
| Citric acid | 1.5 parts |
| Sodium citrate | 0.1 part |
| Vitamin C | 0.15 part |
| Soda pop essence | 1 part |
| Carbonated water | 520 parts |
| Water | 385 parts |

EXAMPLE 4

A jelly composition was prepared according to the following formulation.

| Agar | 4 parts |
|---|---|
| Water | 350 parts |
| Sugar | 125 parts |
| Fruit juice | 150 parts |
| Indigestible dextrin of Reference Example 2 | 10 parts |

EXAMPLE 5

An ice cream composition was prepared according to the following formulation.

| Skim milk powder | 54 parts |
|---|---|
| Sugared condensed whole milk | 176.4 parts |
| Sugared skim milk | 122.4 parts |
| Unsalted butter | 30 parts |
| Water | 700.6 parts |
| Vegetable oil and fat | 36 parts |
| Refined white sugar | 18 parts |
| Starch syrup | 30 parts |
| Indigestible dextrin of Reference Example 3 | 24 parts |
| Emulsifier | 6.2 parts |
| β-Carotene | 0.24 parts |
| Flavor | 1.8 parts |

The carbonated beverage composition of Example 3 was given to 20 hypertensives in an amount of 200g daily for each for 6 months, resulting in reduction of average blood pressure from 111.5±9.7 to 104.8±9.6 mmHg.

The jelly composition of Example 4 were give in an amount of 300g, and ice cream composition of Example 5 were given in an amount of 200g to each 15 hypertensives daily for each for 6 months. This resulted in reduction of average blood pressure from 108.8±8.3 to 103.2±9.2 mmHg.

EXAMPLE 6

6 men (53.2 old in average) were fed on an indigestible dextrin of the Reference Example 1 for 30 days at every 3 times on a day, and checked for blood pressure with time.

Test results were shown in Table 4.

TABLE 4

| I.D. No. | Systolic blood pressure | | Diastolic pressure | |
|---|---|---|---|---|
|  | before test | 1 month after | before test | 1 month after |
| 1 | 131.7 ± 11.2 | 121.0 ± 5.8 | 98.3 ± 11.2 | 88.3 ± 6.7 |

TABLE 4-continued

| I.D. No. | Systolic blood pressure | | Diastolic pressure | |
|---|---|---|---|---|
| | before test | 1 month after | before test | 1 month after |
| 2 | 131.7 ± 18.8 | 129.0 ± 9.5 | 110.3 ± 19.9 | 89.7 ± 16.8 |
| 3 | 139.3 ± 7.2 | 115.0 ± 5.9 | 90.7 ± 7.4 | 77.3 ± 2.0 |
| 4 | 143.7 ± 6.4 | 120.0 ± 5.0 | 103.7 ± 6.2 | 84.7 ± 4.3 |
| 5 | 119.0 ± 3.8 | 108.7 ± 3.5 | 82.0 ± 2.0 | 73.7 ± 5.2 |
| 6 | 128.7 ± 8.4 | 113.0 ± 4.6 | 88.3 ± 4.7 | 76.3 ± 7.2 |
| average ± SEM | 130.9 ± 2.8 | 117.8 ± 2.9 | 95.6 ± 4.3 | 81.7 ± 2.8 |
| | $P < 0.01$ | | $P < 0.05$ | |

What is claimed is:

1. A method for treating hypertension which comprises the steps of:
   (a) providing an indigestible dextrin which is obtained by hydrolyzing pyrodextrin with α-amylase and refining the hydrolyzed pyrodextrin; and
   (b) administering an effective amount of the indigestible dextrin to a mammal.

2. The method of claim 1, wherein said pyrodextrin is prepared by heating starch in the presence of hydrochloric acid.

3. The method of claim 1, wherein said mammal is a human being.

4. The method of claim 3, wherein said indigestible dextrin is administered in the form of food containing the same.

5. A method for treating hypertension which comprises the steps of:
   (a) providing an indigestible dextrin which is obtained by hydrolyzing pyrodextrin with α-amylase and then with glucoamylase, and subjecting the hydrolyzed dextrin to ion exchange resin chromatography to refine the hydrolyzed pyrodextrin; and
   (b) administering an effective amount of the indigestible dextrin to a mammal.

6. The method of claim 5, wherein said pyrodextrin is prepared by heating starch in the presence of hydrochloric acid.

7. The method of claim 5, wherein said ion exchange resin is an alkaline metal type of strongly acidic ion exchange resin.

8. The method of claim 5, wherein said mammal is a human being.

9. The method of claim 8, wherein said indigestible dextrin is administered in the form of food containing the same.

* * * * *